United States Patent [19]
Fröberg et al.

[11] Patent Number: 5,645,577
[45] Date of Patent: Jul. 8, 1997

[54] CONNECTION INDICATOR FOR MEDICAL DEVICE

[75] Inventors: Paul Fröberg, Bromma; Per Frånberg, Stockholm; Kurt Högnelid, Bromma; Fredrik Killander, Täby; Peter Magnusson, Nacka; Per Nyman, Djursholm, all of Sweden

[73] Assignee: Pacesetter AB, Solna, Sweden

[21] Appl. No.: 492,279

[22] Filed: Jun. 19, 1995

[30]       Foreign Application Priority Data

Jun. 29, 1994 [SE] Sweden .................. 9402297

[51] Int. Cl.⁶ .......................... A61N 1/375
[52] U.S. Cl. .......................... 607/37
[58] Field of Search ............. 607/36, 37, 38; 439/490

[56]       References Cited

U.S. PATENT DOCUMENTS

| | | | |
|---|---|---|---|
| 4,084,875 | 4/1978 | Yamamoto | 439/490 |
| 4,245,643 | 1/1981 | Benzing, III et al. | |
| 4,913,147 | 4/1990 | Fahlstrom et al. | |
| 4,934,366 | 6/1990 | Truex et al. | |
| 5,086,773 | 2/1992 | Ware | |
| 5,336,246 | 8/1994 | Dantanarayana | 607/37 |
| 5,370,669 | 12/1994 | Daglow et al. | 607/36 |

FOREIGN PATENT DOCUMENTS

| | | |
|---|---|---|
| 0 303 235 | 2/1989 | European Pat. Off. |
| 0 448 760 | 10/1991 | European Pat. Off. |
| 0 630 662 | 12/1994 | European Pat. Off. |

*Primary Examiner*—William E. Kamm
*Assistant Examiner*—Scott M. Getzow
*Attorney, Agent, or Firm*—Hill, Steadman & Simpson

[57]       ABSTRACT

A device for indicating that an electrode cable is correctly connected to a medical implant for emitting electrical pulses, the implant being equipped with a connection part for the electrode cable's proximal end, has a contact for making electrical connection with the proximal end of the electrode cable and an indicator, the contact electrically causing the indicator to emit at least one indication signal which is perceptible outside of the implant when the electrode cable is correctly attached to the implant.

12 Claims, 2 Drawing Sheets

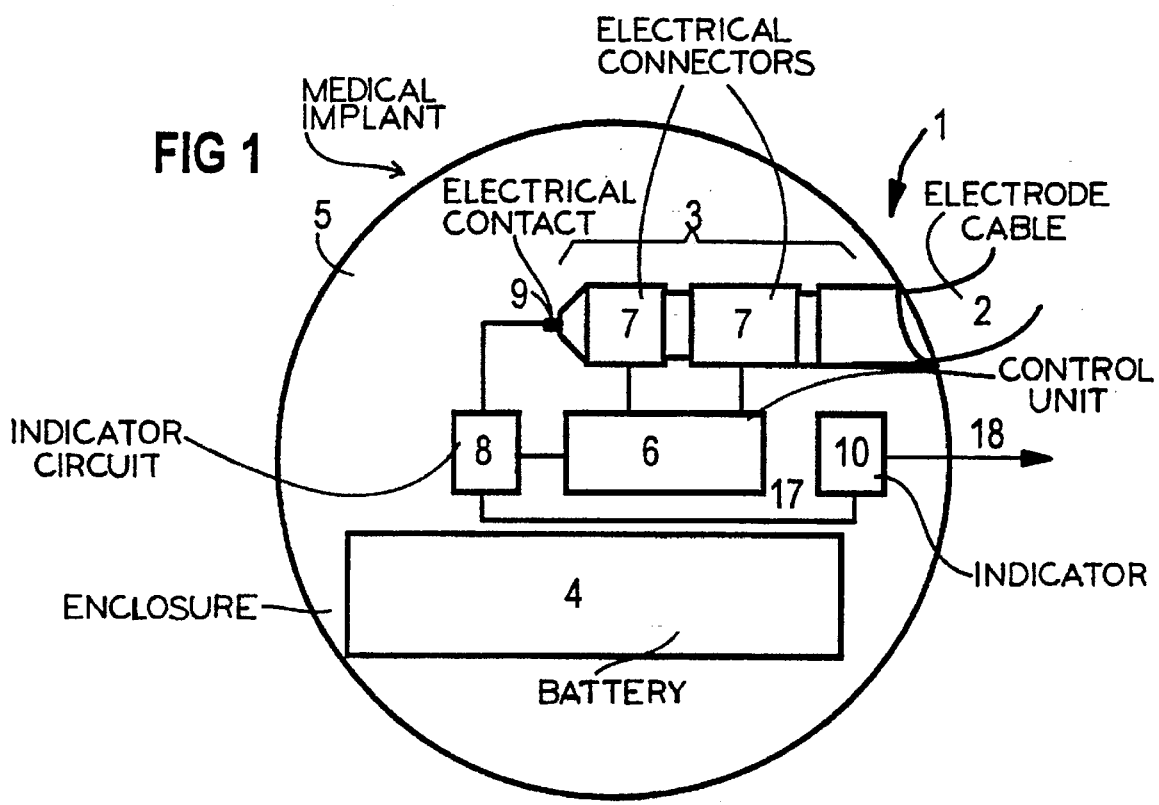
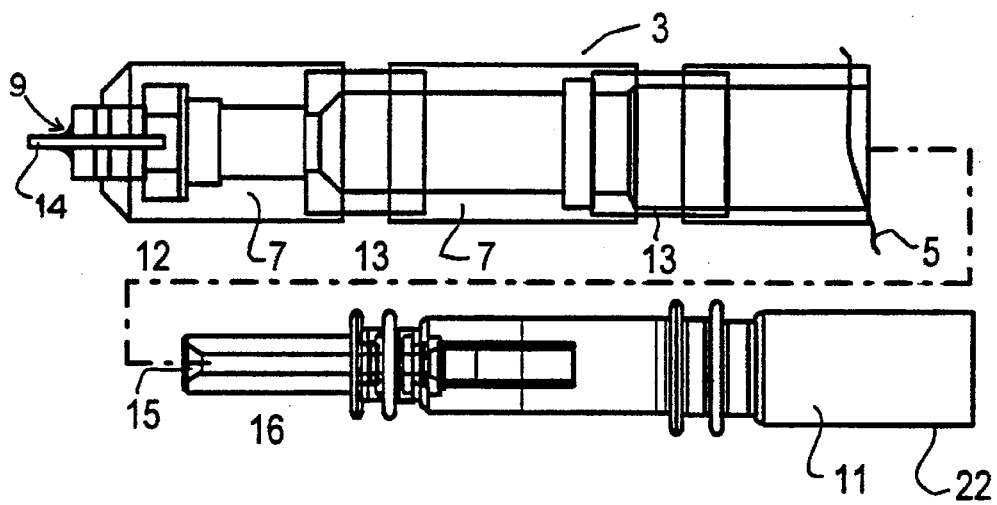

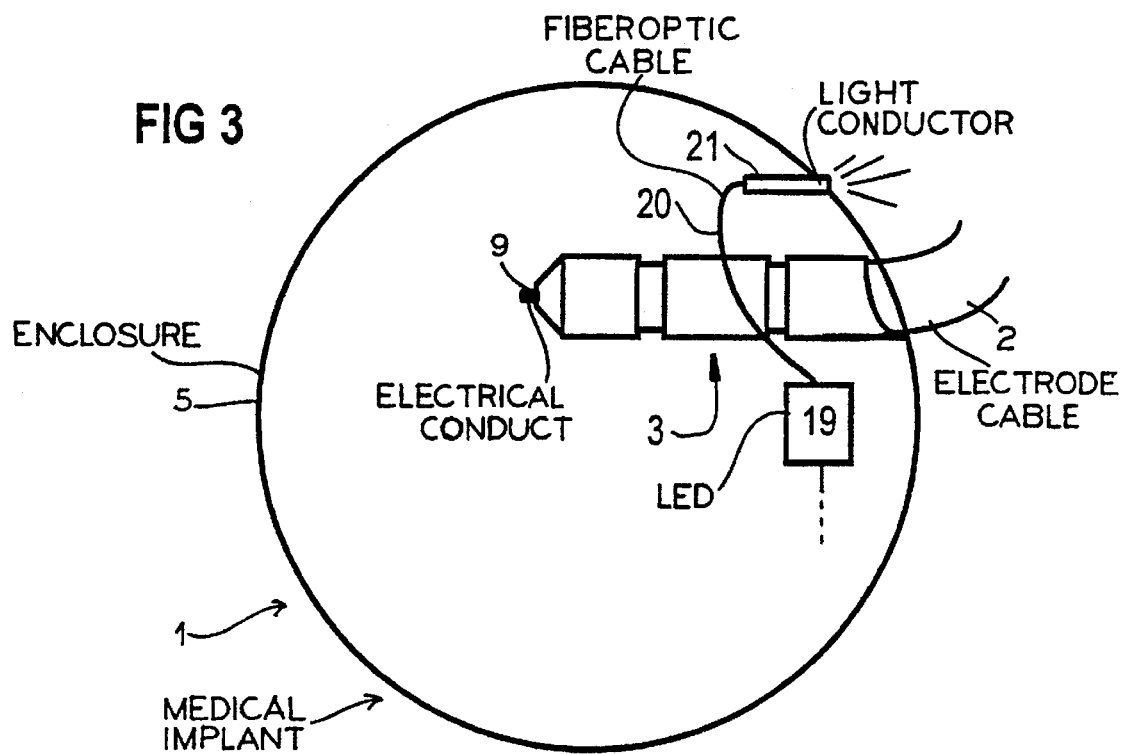
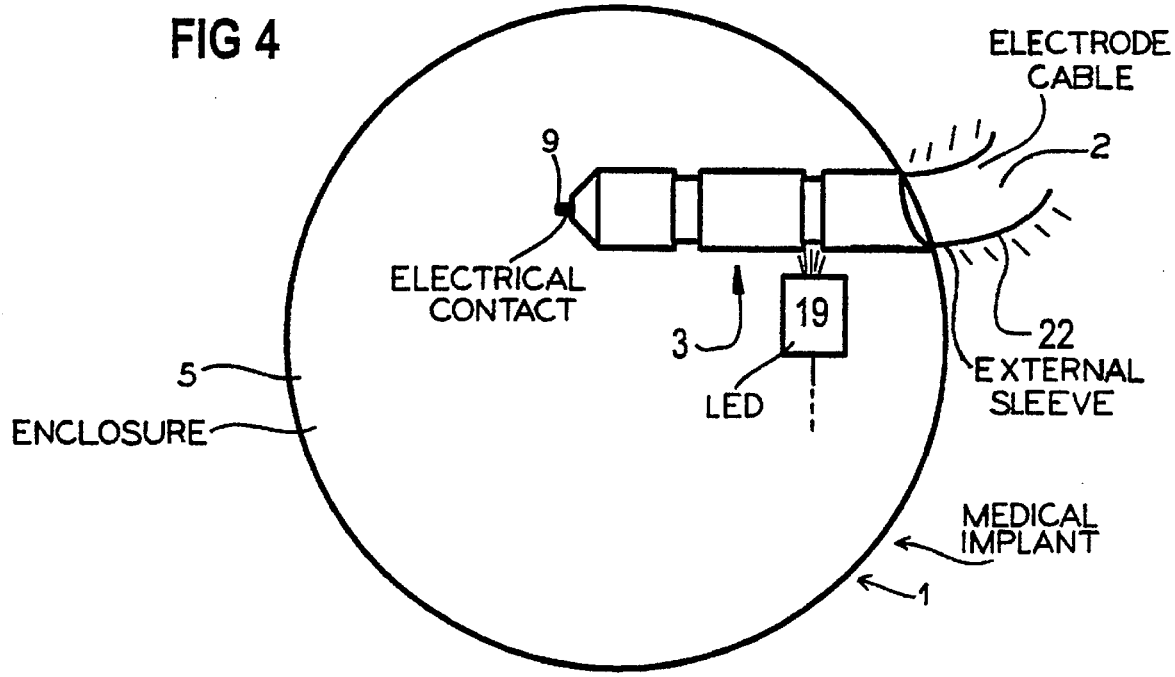

CONNECTION INDICATOR FOR MEDICAL DEVICE

BACKGROUND OF THE INVENTION

1. Field of the Invention

The present invention relates to a device for indicating that an electrode cable is correctly connected to a medical implant for emitting electrical pulses, the implant thereby being equipped with a connection part for the electrode cable's proximal end.

2. Description of the Prior Art

Various types of implantable medical devices are known in the art which include an implant and an electrode cable for delivering electrical energy to a sight within the person in whom the implant is implanted. In such devices, the electrode cable is connected mechanically and electrically to the implant by means of a connector part which contains one or more electrode connectors. In the case of a pacemaker, the connector part is usually a molded part made of transparent epoxy plastic and attached to the top of the metallic pacemaker enclosure. The electrode connectors in the molded part are electrically connected to the pacemaker circuits inside the enclosure via a number of connecting pins. The proximal end of the electrode cable is attached to the molded part with, e.g., screws. U.S. Pat. No. 5,086,773 cites such solutions in a description of the prior art. The device disclosed in U.S. Pat. No. 5,086,773 is an example of an electrode cable attachment arrangement without screws or the need for tools. This known attachment device contains at least one coil spring, arranged in a connection receptacle, for the proximal end of the electrode cable. The internal diameter of the coil spring is slightly smaller than the external diameter of the proximal end. When pressure on the connection part is relaxed, the spring resumes its normal state, thereby affixing the electrode cable and establishing electrical contact.

European Application 448 760 also provides an example of a fixation device in which a spring located in a connection receptacle is employed for attaching and seating an electrical conductor in the connection receptacle.

With electrode connection in a transparent molded part, an external visual check can be made to ensure that the connection is correct. A disadvantage with the use of a molded part of the type described above, however, is that the part takes a relatively long time to make, since the epoxy plastic needs time to cure. Another disadvantage is that cracks could develop in the molded part over time. These disadvantages can be avoided by integrating the connector into the pacemaker enclosure which would thus have a receptacle for the proximal end of the electrode cable. This type of connection is usually referred to as a "black hole" because visual inspection of its interior after the proximal end of the cable has been inserted is not possible.

U.S. Pat. No. 4,934,366 describes a pacemaker connection with a black hole-type electrode connection and shows how the proximal end of the electrode cable is attached to the pacemaker and seals the attachment area without the need for screws. Fixing is achieved using clamping rings, threaded onto the proximal end of the electrode cable when the cable is connected to the pacemaker, and springs surrounding the proximal end, the springs also serving as electrical connectors for the electrode cable.

One problem with black hole connections according of the type described in U.S. Pat. No. 4,934,366 is that no indication is provided as to whether the electrode cable has been correctly attached and seated. Physicians implanting medical implants have expressed a wish for some kind of indication showing that the connection is correct.

One device, which emits a clicking sound to confirm that the electrode cable's proximal end has been correctly connected to a device for emitting electrical pulses, is described in European Application 0 630 662. The mechanically generated clicking noise is produced by a dish-shaped disk which snaps from one position to another when the end of the electrode presses against the disk.

SUMMARY OF THE INVENTION

An object of the present invention is to provide an improved indication device which identifies when a correct connection is made between a proximal end of a cable and an electrical contact in a connection receptacle of a medical implant.

The above object is achieved in accordance with the principals of the present invention in a medical implant having an electrical contact and associated circuitry contained in the enclosure for generating an electrical control signal when the distal end of the electrode cable is correctly inserted in the connector part, and an indicator supplied with said control signal which electrically emits an indicator signal, detectable outside of the implant enclosure, in response to the electrical control signal.

According to a first embodiment, the indication signal is an acoustic signal generated by a piezo-generator in the implant, e.g., a piezo-crystal or piezo-ceramic element.

According to a second embodiment, the indication signal is an optical signal generated by a light-emitting diode located in the implant. The optical signal is carried by a fiberoptic cable to an optical light conductor which transmits the optical signal to the exterior of the implant.

According to a third embodiment, the indication signal again is an optical signal generated by a light emitting diode located in the implant. In this embodiment, the optical signal is carried to the exterior of the implant by the electrode cable's external, transparent sleeve.

According to a fourth embodiment, an indication signal generator generates electrical pulses as the indicator signal which, via a contact for the electrode cable, are supplied to the electrode cable, so pulses emitted from the distal end of the electrode cable can be detected by ECG equipment.

DESCRIPTION OF THE DRAWINGS

FIG. 1 is a schematic illustration of a medical implant with an indicator device constructed according to the present invention which generically illustrates all embodiments.

FIG. 2 is an enlarges schematic illustration of a connection part of a medical implant and an electrode cable forming a part of the indicator device according to the invention.

FIG. 3 is a schematic illustration of the aforementioned second embodiment of the invention.

FIG. 4 is a schematic illustration of the aforementioned third embodiment of the invention.

DESCRIPTION OF THE PREFERRED EMBODIMENT

The invention will be described referring to a medical implant for connection of only one electrode cable. The invention is, however, also applicable to medical implants accepting two or more connected electrode cables.

The medical implant could be, e.g., a pacemaker, a defibrillator or a nerve stimulator.

FIG. 1 shows a schematic illustration of a medical implant 1 having a connection part 3 and a battery 4 for powering the implant 1. An electrode cable 2 is shown connected to the connection part 3. The implant 1 further has an enclosure 5 and a control unit 6 for controlling operation of the implant 1, connected to one or a number of connectors 7 in the connection part 3. The control device 6 is also connected to an indication circuit 8 and to a contact 9, located in the connection part 3. The indication circuit 8, the contact 9 and an indicator 10 jointly constitute the indication device 10 according to the invention in this embodiment. The indicator 10 is electrically connected to the indication circuit 8.

The description of the invention below refers to both FIG. 1 and FIG. 2.

FIG. 2 shows a more detailed schematic illustration of the connection part 3 and the proximal end 11 of the electrode cable 2. The connection part 3 has a fixing device 12 for attaching the proximal end 11 of the electrode cable and one or a more insulated segments 13 which can be made of a transparent ceramic. The fixing device 12 may be a coiled spring concentrically arranged in the connection part 3 inside the connection means 7. The internal diameter of the spring is only slightly smaller than the diameter of the outermost part 16 of the proximal end 11 of the electrode cable. The term "outermost part of the proximal end of the electrode cable" refers to the cable portion which is deepest inside the connection part 3 when connection is correct. The electrode cable 2 is attached to the implant 1 when the proximal end is rotated by a part of one turn in the coil spring's coiling direction at the same time as the end is pushed into the connection part 3. This rotation causes the spring to expand enough to permit insertion of the electrode cable's proximal end 11. When rotation ceases and pressure on the electrode cable 2 is relaxed, the spring strives to resume its normal state, thereby attaching the proximal end 11 of the electrode cable in the connection part 3.

The contact 9 inside the connection part 3 is equipped with a pin 14, concentrically arranged inside the connection part 3, arranged such that the pin 14 is inserted into an opening 15 in the outermost part 16 of the proximal end 11 of the electrode cable when the electrode cable 2 is attached, electrical contact thereby being established between the pin 14 of the contact, the outermost part 16 of the proximal end 11 of the electrode cable, the fixing device 12 and the connectors 7. When the electrode cable 2 has been mechanically affixed by the fixing device 12 and electrically connected with the connectors 7, the contact 9 with its pin 14 and the indication circuit 8 as well have a potential thereacross applied by the control unit 6 to the connectors 7. This is detected by the indication circuit 8 which generates a control signal 17 supplied to the indicator 10 in which an indication signal 18, perceptible outside the medical implant 1, is generated.

According to a first embodiment, the indication signal 18 is an acoustic signal generated by a piezo-generator as the indicator 10, e.g., a piezo-crystal or piezo-ceramic element. In a pacemaker with an activity sensor consisting of a piezo-crystal, this crystal also can be used as the indicator 10 for sound generation. The piezo-generator can, e.g., be glued to the inside of the implant enclosure 5 or can be located in the implant 1 on a carrier for the components therein. The indication signal 18 can, e.g., consist of two brief acoustic signals occurring ten seconds after the electrode cable 2 has been correctly connected to the implant.

FIG. 3 shows a second embodiment in which the indicator 10 is a light-emitting diode 19, the indication signal 18 then being an optical signal generated by the light-emitting diode 19. The optical signal is carried by a fiberoptic cable 20 to an optical light conductor 21 which transmits the optical signal to the exterior of the implant 1. The light conductor 21 can, e.g., be a sapphire pin arranged in the connection part 3 between the interior and the exterior of the implant 1. The indication signal 18 can, e.g., consist of two brief light blinks ten seconds after the electrode cable 2 has been correctly connected to the implant 1.

FIG. 4 shows a third embodiment in which the indicator 10 is a light-emitting diode 19, as in the second preferred embodiment, the indication signal 18 in this embodiment again being an optical signal generated by the light emitting diode 19. The light-emitting diode 19 is positioned so it can illuminate one of the insulated segments 13 arranged on the connection part 3. In this third embodiment, the insulated segments 13 are made of a transparent material, e.g., a transparent ceramic. The light-emitting diode 19 illuminates the insulated segment 13 nearest the enclosure 5 of the implant 1. When the electrode cable 2 has been correctly connected, the insulating outer sleeve 22 of the electrode cable 2, which is made of, e.g., a transparent silicone plastic, is adjacent to the insulated segment 13, the silicone plastic then serving as a light conductor so the optical signal generated by the light emitting diode 19 is carried, via the insulated segment 13 and the external sleeve 22 of the electrode cable 2, to the exterior of the implant 1 where the indication signal 18 is visible in the electrode sleeve 22 next to the implant 1. The indication signal 18 can, e.g., consist of two brief light blinks ten seconds after the electrode cable 2 has been correctly connected to the implant 1.

According to a fourth embodiment, the indicator 10 generates electrical pulses which, via the contact 9, are applied to the electrode cable 2 and carried to the electrode cable's 2 distal end located, e.g., inside the heart of a patient. The pulses sent to the electrode cable 2 via the contact 9 can be detected with ECG equipment which is always available for monitoring the patient's ECG during an implantation. According to one alternative, two closely spaced consecutive pulses are sent to the contact 9 and are carried to the distal end of the electrode cable 2, thereby making it easy to identify the pulses with ECG equipment and supply an indication that connection is correct. According to another alternative, a pulse is sent to the contact 9. The control unit 6 then sends a pulse shortly thereafter to one of the connectors 7. Identification of the pulses with ECG equipment supplies an indication showing that the connection is correct. After a defined period of time, e.g., thirty seconds after the electrode cable 2 has been connected, the indication circuit 8 stops generating pulses.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a medical implant system having an enclosure, an electrode cable having a proximal end, and a connector part attached to said enclosure in which said proximal end of said electrode cable is inserted, the improvement of a device for indicating when said proximal end of said cable is correctly inserted in said connector part, comprising:

means in said enclosure for generating an electrical control signal when said proximal end of said electrode cable is correctly inserted in said connector part; and an indicator in said enclosure supplied with said control signal which electrically emits an indicator signal, detectable outside of said enclosure, in response to said control signal, said indicator comprising a light-emitting diode disposed in said enclosure and a light-conductor having an end disposed at an exterior of said enclosure, said light-emitting diode emitting light in response to said control signal.

2. The improvement of claim 1 wherein said means for generating an electrical control signal includes an electrical contact disposed in said connector part which makes an electrical connection with said proximal end of said electrode cable only if said proximal end of said electrode cable is correctly inserted in said connection part.

3. The improvement of claim 1 further comprising fixing means in said connector part for receiving said proximal end of said electrode cable and, when said electrode cable is correctly inserted, causing said electrode cable to be in electrical connection with said electrical contact.

4. The improvement of claim 2 wherein said connector part includes at least one electrical connector forming a circuit with said electrical contact which is completed when said proximal end of said electrode cable is correctly inserted in said connector part, said means for generating said electrical control signal generating said electrical control signal when said circuit is completed.

5. In a medical implant system having an enclosure, an electrode cable having a proximal end, and a connector part attached to said enclosure in which said proximal end of said electrode cable is inserted, the improvement of a device for indicating when said proximal end of said cable is correctly inserted in said connector part, comprising;

means in said enclosure for generating an electrical control signal when said proximal end of said electrode cable is correctly inserted in said connector part; and an indicator in said enclosure supplied with said control signal which electrically emits an indicator signal, detectable outside of said enclosure, in response to said control signal, said indicator comprising a light-emitting diode disposed in said enclosure adjacent said electrode cable, and said indicator further comprising a component of said electrode cable containing a light-conducting element for transmitting light emitted by said light-emitting diode in response to said control signal to an exterior of said enclosure.

6. The improvement of claim 5 wherein said means for generating an electrical control signal includes an electrical contact disposed in said connector part which makes an electrical connection with said proximal end of said electrode cable only if said proximal end of said electrode cable is correctly inserted in said connection part.

7. The improvement of claim 5 further comprising fixing means in said connector part for receiving said proximal end of said electrode cable and, when said electrode cable is correctly inserted, causing said electrode cable to be an electrical connection with said electrical contact.

8. The improvement of claim 7 wherein said connector part includes at least one electrical connector forming a circuit with said electrical contact which is completed when said proximal end of said electrode cable is correctly inserted in said connector part, said means for generating said electrical control signal generating said electrical control signal when said circuit is completed.

9. In a medical implant system having an enclosure, an electrode cable having a proximal end, and a connector part attached to said enclosure in which said proximal end of said electrode cable is inserted, the improvement of a device for indicating when said proximal end of said cable is correctly inserted in said connector part, comprising;

means in said enclosure for generating an electrical control signal when said proximal end of said electrode cable is correctly inserted in said connector part; and an indicator in said enclosure supplied with said control signal which electrically emits an indicator signal, detectable outside of said enclosure, in response to said control signal, said indicator comprising means for generating electrical pulses and for supplying these pulses via said electrode cable to a location at an exterior of said enclosure, said pulses being detectable with ECG equipment.

10. The improvement of claim 9 wherein said means for generating an electrical control signal includes an electrical contact disposed in said connector part which makes an electrical connection with said proximal end of said electrode cable only if said proximal end of said electrode cable is correctly inserted in said connection part.

11. The improvement of claim 9 further comprising fixing means in said connector part for receiving said proximal end of said electrode cable and, when said electrode cable is correctly inserted, causing said electrode cable to be an electrical connection with said electrical contact.

12. The improvement of claim 11 wherein said connector part includes at least one electrical connector forming a circuit with said electrical contact which is completed when said proximal end of said electrode cable is correctly inserted in said connector part, said means for generating said electrical control signal generating said electrical control signal when said circuit is completed.

* * * * *